(12) United States Patent
Kanayama et al.

(10) Patent No.: US 6,720,288 B1
(45) Date of Patent: Apr. 13, 2004

(54) HERBICIDAL COMPOSITIONS AND METHOD OF USING THE SAME

(75) Inventors: Masahiro Kanayama, Nagaokakyo (JP); Tsutomu Mabuchi, Osakasayama (JP); Takashi Ohtsuka, Tondabayashi (JP); Sumitaka Kose, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/069,032

(22) PCT Filed: Aug. 23, 2000

(86) PCT No.: PCT/JP00/05632

§ 371 (c)(1),
(2), (4) Date: May 28, 2002

(87) PCT Pub. No.: WO01/13729

PCT Pub. Date: Mar. 1, 2001

(30) Foreign Application Priority Data

Aug. 23, 1999 (JP) .......................................... 11-235423

(51) Int. Cl.⁷ ...................... A01N 43/56; A01N 57/02
(52) U.S. Cl. ...................... 504/128; 504/139; 504/206; 504/282
(58) Field of Search ................................ 504/128, 139, 504/206, 282

(56) References Cited

U.S. PATENT DOCUMENTS

| | | | |
|---|---|---|---|
| 4,080,191 A | 3/1978 | Harvey | 71/92 |
| 6,248,695 B1 * | 6/2001 | Griffiths et al. | 504/206 |

FOREIGN PATENT DOCUMENTS

| | | |
|---|---|---|
| EP | 0325054 A | 7/1989 |
| EP | 0595126 A | 5/1994 |
| EP | 0862857 A | 9/1998 |
| JP | 60-75324 A | 4/1985 |
| JP | 7-242510 A | 9/1995 |
| WO | WO98/29554 | 7/1998 |

OTHER PUBLICATIONS

Anderson et al. (1994) ACS Symposium Series, vol. 559, Porphyric Pesticides, S.O. Duke and C.A. Robeiz eds. pp. 18–33.

* cited by examiner

*Primary Examiner*—S. Mark Clardy
(74) *Attorney, Agent, or Firm*—Collard & Roe, P.C.

(57) ABSTRACT

Herbicidal compositions containing as the active ingredients (one or more compounds selected from among light-induced herbicidal compounds and one or more compounds selected from among organoposphorus herbicidal compounds, characterized by containing ethylenediamine alkoxylates and alcohol alkoxylates as surfactants. These herbicidal compositions have an excellent rapid action and exert a remarkable herbicidal effect in a small dose.

11 Claims, No Drawings

HERBICIDAL COMPOSITIONS AND METHOD OF USING THE SAME

CROSS REFERENCE TO RELATED APPLICATIONS

Applicants claim priority under 35 U.S.C. §119 of JAPANESE Application No. 11-235423 filed on Aug. 23, 1999. Applicants also claim priority under 35 U.S.C. §365 of PCT/JP00/05632 filed on Aug. 23, 2000. The international application under PCT article 21(2) was not published in English.

TECHNICAL FIELD

This invention relates to a herbicidal composition having a rapid action, an improved effect and a long-term stability of preparation.

BACKGROUND ART

Among the light-induced herbicidal compositions represented by the general formula (I), the 3-substituted phenylpyrazole derivatives represented by the general formula (I-1) are known compounds disclosed in JP-A-3-163063 and JP-A-4-211065, wherein it is mentioned that these compounds have, as herbicides for foliage treatment, an outstanding herbicidal activity on the general broad-leaved weeds noxious in the upland farming.

It is known that a similar herbicidal activity is exhibited by a number of compounds resembling the general formula (I-1) in the over-all chemical structure and relative configuration of substituents used as light-induced or protox-inhibiting herbicides [Anderson et al., ACS Symposium Series, Vol. 559, Porphyric Pesticides, S. O. Duke and C. A. Robeiz eds., p.18–34 (1994)]. It is also known that a resistance to these light-induced herbicides can generally be given to plants by introducing a specific gene into the plants (International Patent Application WO98/29554).

On the other hand, organophosphorus herbicidal compounds such as the N-(phosphonomethyl)-glycine or salts thereof disclosed in JP-A-47-39538 and JP-A-57-95994, the 4-[hydroxy(methyl)phosphino]-DL-homoalanine or salts thereof disclosed in JP-A-57-26564 and the 4-[hydroxy(methyl)phosphino]-L-homoalany-L-alanyl-L-alanine or salts thereof disclosed in JP-A-50-23282, etc. are well known as non-selective herbicides for foliage treatment.

Further, JP-A-7-242510 discloses herbicidal compositions containing a 3-substituted phenylpyrazole derivative and an organophosphorus herbicidal compound.

Further, Weed Sci. Soc. 25, (1977), p.275–287 refers to the adjuvant effect of alcohol alkoxylates on N-(phosphonomethyl)glycine. However, this technique is insufficient in the adjuvant effect and the alcohol alkoxylates are not readily compatible with aqueous solution of N-(phosphonomethyl)glycine.

Thus, it has been demanded to improve the herbicidal effect and rapid action of a herbicidal composition containing a light-induced herbicidal compound (especially a 3-substituted phenylpyrazine derivative) and an organophosphorus herbicidal compound.

The present inventors have conducted extensive studies with the aim of solving the problems mentioned above to find that, by adding an ethylenediamine alkoxylate and an alcohol alkoxylate as surfactants to a herbicidal composition containing one or more compounds selected from light-induced herbicidal compounds, especially one or more compounds selected from the 3-substituted phenylpyrazole derivatives represented by the general formula (I-1), and organophosphorus herbicidal compounds as active ingredients, the rapid action of the composition can be made excellent and the effect of the composition can be improved by the synergistic action of the active ingredients and the surfactants, besides there can be obtained a herbicidal composition keeping stable for a long period of time. Based on this finding, this invention has been accomplished.

DISCLOSURE OF THE INVENTION

The present invention relates to a herbicidal composition containing one or more compounds selected from light-induced herbicidal compounds and one more compounds selected from organic herbicidal compounds as active ingredients; and containing an ethylenediamine alkoxylate and an alcohol alkoxylate as surfactants.

Particularly, the present invention relates to a herbicidal composition containing, as active ingredients, one or more compounds selected from the group consisting of the compounds represented by the following general formula (I): wherein P represents $P^1$ to $P^9$:

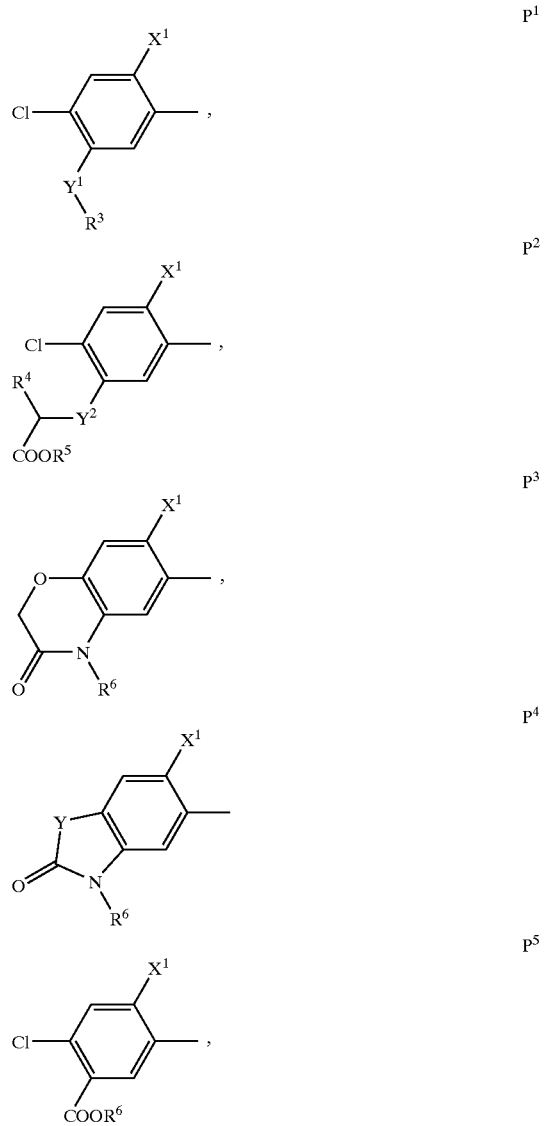

P6 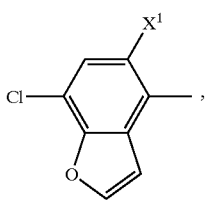

P7 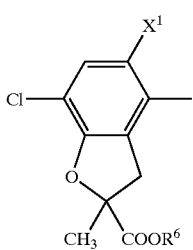

P8 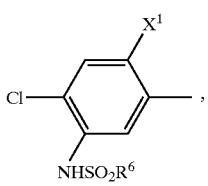

P9 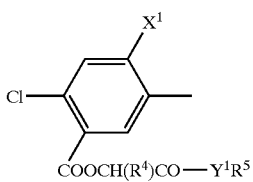

wherein $X^1$, $Y$, $Y^1$, $Y^2$, $R^3$, $R^4$, $R^5$ and $R^6$ are as defined below, and Q represents $Q^1$ to $Q^{11}$:

Q1 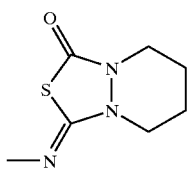

Q2 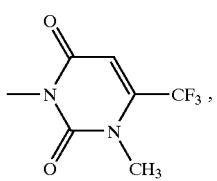

Q3 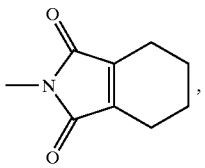

Q4 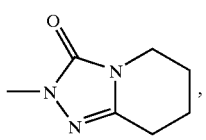

Q5 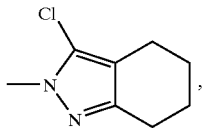

Q6 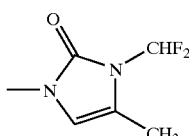

Q7 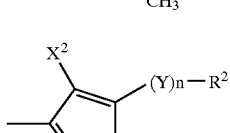

Q8 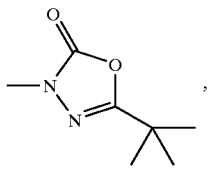

Q9 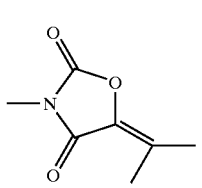

Q10 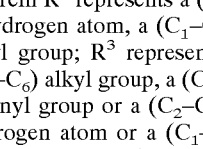

Q11 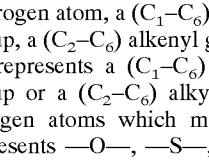

wherein $R^1$ represents a $(C_1-C_6)$ alkyl group; $R^2$ represents a hydrogen atom, a $(C_1-C_6)$ alkyl group or a halo $(C_1-C_6)$ alkyl group; $R^3$ represents a $(C_1-C_6)$ alkyl group, a halo $(C_1-C_6)$ alkyl group, a $(C_3-C_6)$ cycloalkyl group, a $(C_2-C_6)$ alkenyl group or a $(C_2-C_6)$ alkynyl group; $R^4$ represents a hydrogen atom or a $(C_1-C_6)$ alkyl group; $R^5$ represents a hydrogen atom, a $(C_1-C_6)$ alkyl group, a halo $(C_1-C_6)$ alkyl group, a $(C_2-C_6)$ alkenyl group or a $(C_2-C_6)$ alkynyl group; $R^6$ represents a $(C_1-C_6)$ alkyl group, a $(C_2-C_6)$ alkenyl group or a $(C_2-C_6)$ alkynyl group; $X^1$ and $X^2$ represent halogen atoms which may be the same or different; Y represents —O—, —S—, —SO— or —$SO_2$—; $Y^1$ represents —O— or —S—; $Y^2$ represents —O—, —S— or —NH—; and n represents an integer of 0 to 1;

and more particularly, one or more compounds selected from the group consisting of the 3-substituted phenylpyrazole derivatives represented by the following general formula (I-1):

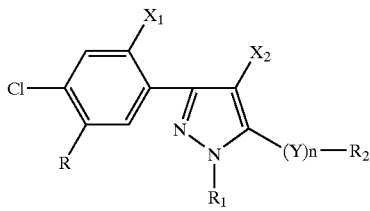

(I-1)

wherein R represents —$Y^1$—$R^3$ (wherein $R^3$ represents a ($C_1$–$C_6$) alkyl group, a halo ($C_1$–$C_6$) alkyl group, a ($C_2$–$C_6$) alkenyl group or a ($C_2$–$C_6$) alkynyl group; and $Y^1$ represents —O— or —S—), —$Y^2$CH($R^4$)CO—$OR^5$ (wherein $R^4$ represents a hydrogen atom or a ($C_1$–$C_6$) alkyl group; $R^5$ represents a hydrogen atom, a ($C_1$–$C_6$) alkyl group, halo ($C_1$–$C_6$) alkyl group, a ($C_2$–$C_6$) alkenyl group or a ($C_2$–$C_6$) alkynyl group; and $Y^2$ represents —O—, —S— or —NH—), —COOCH($R^4$)CO—$Y^1$ $R^5$ (wherein $R^4$, $R^5$ and $Y^1$ are as defined above), or —$COOR^6$ (wherein $R^6$ represents a ($C_1$–$C_6$) alkyl group, a ($C_2$–$C_6$) alkenyl group or a ($C_2$–$C_6$) alkynyl group); $R^1$ represents a ($C_1$–$C_6$) alkyl group; $R^2$ represents a hydrogen atom, a ($C_1$–$C_6$) alkyl group or a halo ($C_1$–$C_6$) alkyl group; $X^1$ and $X^2$ represent halogen atoms which may be the same or different; Y represents —O—, —S—, —SO— or —$SO_2$—; and n represents an integer of 0 to 1; and one or more compounds selected from the group consisting of organophosphorus herbicidal compounds, and further containing, as surfactants, an ethylenediamine alkoxylate and an alcohol alkoxylate.

MODE FOR CARRYING OUT THE INVENTION

Among the substituents in the general formula (I) and general formula (I-1), the term "($C_1$–$C_6$) alkyl group" means a straight or branched chain alkyl group having 1–6 carbon atoms such as methyl, ethyl, n-propyl, i-propyl, n-butyl, i-butyl, s-butyl, t-butyl, n-pentyl, n-hexyl and the like; "halo ($C_1$–$C_6$) alkyl group" means a straight or branched chain alkyl group having 1–6 carbon atoms substituted with one or more halogen atoms which are selected from the group consisting of chlorine atom, fluorine atom, iodine atom and bromine atom and may be the same or different; "($C_2$–$C_6$) alkenyl group" means a straight or branched chain alkenyl group having 2–6 carbon atoms; and "($C_2$–$C_6$) alkynyl group" means a straight or branched chain alkynyl group having 2–6 carbon atoms.

As examples of the light-induced herbicidal compounds of this invention, the following ones can be referred to:

(1) 3-(4-Chloro-5-(cyclopentyloxy)-2-fluorophenyl)-5-isopropylidene-1,3-oxazolidindione (general name: pentoxazone)

(2) Pentyl [2-chloro-5-(cyclohexa-1-ene-1,2-dicarboximide)-4-fluorophenoxy]-acetate (general name: flumiclorac-pentyl)

(3) 7-Fluoro-6-[(3,4,5,6-tetrahydro)phthalimido]-4-(2-propynyl)-1,4-benzoxazin-3(2H)-one (general name: flumioxazin)

(4) Ethyl (RS)-2-chloro-3-[2-chloro-5-(4-fluoromethyl-4,5-dihydro-3-methyl-5-oxo-1H-1,2,4-triazol-1-yl)-4-fluorophenyl]propionate (general name: carfentrazone-ethyl)

(5) 2',4'-Dichloro-5'-(4-difluoromethyl-4,5-dihydro-3-methyl-5-oxo-1H-1,2,4-triazol-1-yl)-methane-sulfonanilide (general name: sulfentrazone)

(6) 2-(2,4-Dichloro-5-propyn-2-yloxyphenyl)-5,6,7,8-tetrahydro-1,2,4-triazolo[4,3-a]pyridin-3(2H)-one (general name: azafenidin)

(7) 5-tert-Butyl-3-[2,4-dichloro-5-(propyn-2-yloxy)phenyl]-1,3,4-oxadiazole (general name: oxadiargyl)

(8) 5-tert-Butyl-3-(2,4-dichloro-5-isopropoxy-phenyl)-1,3,4-oxadiazol-2(3H)-one (general name: oxadiazon)

(9) Methyl [2-chloro-4-fluoro-5-(5,6,7,8-tetrahydro-3-oxo-1H,3H-[1,3,4]thiadiazolo[3,4-a]pyriadzin-1-ylideneamino)phenylthio]acetate (general name: fluthacet-methyl) etc.

As the compound groups exhibiting a similar activity, the following diphenyl ether type compounds are known:

nitrofen (general name), bifenox (general name), oxyfluorfen (general name), acifluorfen (general name), fomesafen (general name), etc. Besides above, the following 3-substituted phenylpyrazole derivatives represented by the general formula (I-1) can also be referred to:

General Formula (I-1)

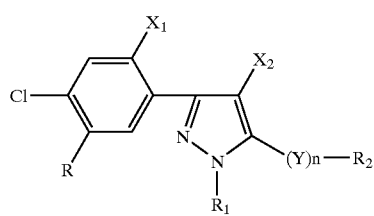

(I-1)

TABLE 1

| | | ($R_1$ = $CH_3$) | | | | |
|---|---|---|---|---|---|---|
| No. | R | $R_2$ | $X_1$ | $X_2$ | (Y)n | Property |
| 1 | $OCH_2CH=CH_2$ | $CH_3$ | Cl | Cl | S | nD 1.6131(25.3° C.) |
| 2 | $OCH_2CH=CH_2$ | $CHF_2$ | Cl | Cl | O | nD 1.5536(28.4° C.) |
| 3 | $OCH_2CH=CH_2$ | $CHF_2$ | F | Cl | O | m.p. 63.7–64.1° C. |
| 4 | $SCH_2CH=CH_2$ | $CH_3$ | Cl | Cl | S | Paste |
| 5 | $SCH_2CH=CH_2$ | $CHF_2$ | Cl | Cl | O | m.p. 52.0–55.0° C. |
| 6 | $SCH_2CH=CH_2$ | $CHF_2$ | F | Cl | O | nD 1.5670(17.9° C.) |
| 7 | $OCH_2C\equiv CH$ | $CH_3$ | Cl | Cl | S | m.p. 71.5° C. |
| 8 | $OCH_2C\equiv CH$ | $CHF_2$ | Cl | Cl | O | m.p. 84.0° C. |

TABLE 1-continued ($R_1 = CH_3$)

| No. | R | $R_2$ | $X_1$ | $X_2$ | (Y)n | Property |
|---|---|---|---|---|---|---|
| 9 | OCH$_2$C≡CH | CHF$_2$ | F | Cl | O | m.p. 98.0–98.1° C. |
| 10 | SCH$_2$C≡CH | CH$_3$ | Cl | Cl | S | m.p. 94.5° C. |
| 11 | SCH$_2$C≡CH | CHF$_2$ | Cl | Cl | O | m.p. 127–129° C. |
| 12 | SCH$_2$C≡CH | CHF$_2$ | F | Cl | O | m.p. 82.8° C. |
| 13 | OCH$_2$COOCH$_3$ | CH$_3$ | Cl | Cl | S | m.p. 126.2° C. |
| 14 | OCH$_2$COOCH$_3$ | CHF$_2$ | Cl | Cl | O | m.p. 119.8° C. |
| 15 | OCH$_2$COOCH$_3$ | CHF$_2$ | Cl | Br | O | m.p. 133.8° C. |
| 16 | OCH$_2$COOCH$_3$ | CHF$_2$ | F | Cl | O | m.p. 122.8–123.1° C. |
| 17 | OCH$_2$COOC$_2$H$_5$ | CH$_3$ | Cl | Cl | S | m.p. 106.5° C. |
| 18 | OCH$_2$COOC$_2$H$_5$ | CHF$_2$ | Cl | Cl | O | m.p. 102.3° C. |
| 19 | OCH$_2$COOC$_2$H$_5$ | CHF$_2$ | F | Cl | O | m.p. 127.6° C. |
| 20 | OCH$_2$COOC$_3$H$_7$-n | CHF$_2$ | Cl | Cl | O | m.p. 89.7° C. |
| 21 | OCH$_2$COOC$_3$H$_7$-n | CHF$_2$ | F | Cl | O | m.p. 97.6–97.8° C. |
| 22 | OCH$_2$COOC$_3$H$_7$-i | CHF$_2$ | Cl | Cl | O | m.p. 106.0° C. |
| 23 | OCH$_2$COOC$_3$H$_7$-i | CHF$_2$ | F | Cl | O | m.p. 120.3–120.5° C. |
| 24 | OCH$_2$COOCH$_2$CH=CH$_2$ | CHF$_2$ | Cl | Cl | O | m.p. 84.7° C. |
| 25 | OCH$_2$COOCH$_2$CH=CH$_2$ | CHF$_2$ | F | Cl | O | m.p. 89.2–89.4° C. |
| 26 | OCH$_2$COOCH$_2$C≡CH | CHF$_2$ | Cl | Cl | O | m.p. 119.6° C. |
| 27 | OCH$_2$COOCH$_2$C≡CH | CHF$_2$ | F | Cl | O | m.p. 99.0° C. |
| 28 | OCH(CH$_3$)COOH | CH$_3$ | Cl | Cl | S | m.p. 191–194° C. |
| 29 | OCH(CH$_3$)COOCH$_3$ | CH$_3$ | Cl | Cl | S | m.p. 90–93° C. |
| 30 | OCH(CH$_3$)COOCH$_3$ | CHF$_2$ | F | Cl | O | m.p. 95.6° C. |
| 31 | OCH(CH$_3$)COOC$_2$H$_5$ | CH$_3$ | Cl | Cl | S | nD 1.5763(28.8° C.) |
| 32 | OCH(CH$_3$)COOC$_2$H$_5$ | CHF$_2$ | Cl | Cl | O | nD 1.5238(25.7° C.) |
| 33 | OCH(CH$_3$)COOC$_2$H$_5$ | CHF$_2$ | Cl | Br | O | nD 1.5396(20.8° C.) |
| 34 | OCH(CH$_3$)COOC$_2$H$_5$ | CHF$_2$ | F | Cl | O | m.p. 67.0–67.2° C. |
| 35 | OCH(CH$_3$)COOC$_3$H$_7$-i | CH$_3$ | Cl | Cl | S | m.p. 87–90° C. |
| 36 | SCH(CH$_3$)COOCH$_3$ | CHF$_2$ | Cl | Cl | O | nD 1.5654(19.8° C.) |
| 37 | SCH(CH$_3$)COOCH$_3$ | CHF$_2$ | F | Cl | O | nD 1.5494(25.0° C.) |
| 38 | SCH(CH$_3$)COOC$_2$H$_5$ | CHF$_2$ | Cl | Cl | O | nD 1.5565(28.0° C.) |
| 39 | SCH(CH$_3$)COOC$_2$H$_5$ | CHF$_2$ | F | Cl | O | nD 1.5328(18.0° C.) |
| 40 | NHCH(CH$_3$)COOCH$_3$ | CH$_3$ | Cl | Cl | S | m.p. 144.2° C. |
| 41 | NHCH(CH$_3$)COOC$_2$H$_5$ | CH$_3$ | Cl | Cl | S | Paste |
| 42 | NHCH(CH$_3$)COOC$_2$H$_5$ | CHF$_2$ | Cl | Cl | O | nD 1.5371(23.4° C.) |
| 43 | NHCH(CH$_3$)COOC$_2$H$_5$ | CHF$_2$ | F | Cl | O | nD 1.5264(26.6° C.) |
| 44 | COOCH$_2$COOCH$_3$ | CHF$_2$ | Cl | Cl | O | m.p. 74.4° C. |
| 45 | COOCH$_2$COOCH$_3$ | CHF$_2$ | F | Cl | O | m.p. 1.5350(27.3° C.) |
| 46 | COOCH$_2$COSCH$_3$ | CHF$_2$ | Cl | Cl | O | |
| 47 | COOCH$_2$COSCH$_3$ | CHF$_2$ | F | Cl | O | |
| 48 | COOCH$_2$COOC$_2$H$_5$ | CHF$_2$ | Cl | Cl | O | m.p. 57.2° C. |
| 49 | COOCH$_2$COOC$_2$H$_5$ | CHF$_2$ | F | Cl | O | nD 1.5362(23.4° C.) |
| 50 | COOCH$_2$COSC$_2$H$_5$ | CHF$_2$ | Cl | Cl | O | nD 1.5763(20.7° C.) |
| 51 | COOCH$_2$COSC$_2$H$_5$ | CHF$_2$ | F | Cl | O | nD 1.5536(27.3° C.) |
| 52 | COOCH$_2$COOC$_3$H$_7$-i | CHF$_2$ | Cl | Cl | O | nD 1.5289(24.0° C.) |
| 53 | COOCH$_2$COOC$_3$H$_7$-i | CHF$_2$ | F | Cl | O | |
| 54 | COOCH$_2$COSC$_3$H$_7$-i | CHF$_2$ | Cl | Cl | O | nD 1.5684(20.2° C.) |
| 55 | COOCH$_2$COSC$_3$H$_7$-i | CHF$_2$ | F | Cl | O | |
| 56 | COOCH$_2$COOCH$_2$CH=CH$_2$ | CHF$_2$ | Cl | Cl | O | m.p. 45.4° C. |
| 57 | COOCH$_2$COOCH$_2$CH=CH$_2$ | CHF$_2$ | F | Cl | O | |
| 58 | COOCH$_2$COOCH$_2$C≡CH | CHF$_2$ | Cl | Cl | O | m.p. 79.3° C. |
| 59 | COOCH$_2$COOCH$_2$C≡CH | CHF$_2$ | F | Cl | O | |
| 60 | COOCH(CH$_3$)COOCH$_3$ | CHF$_2$ | Cl | Cl | O | nD 1.5370(25.7° C.) |
| 61 | COOCH(CH$_3$)COOCH$_3$ | CHF$_2$ | F | Cl | O | nD 1.5314(23.0° C.) |
| 62 | COOCH(CH$_3$)COOC$_2$H$_5$ | CHF$_2$ | Cl | Cl | O | nD 1.5672(26.0° C.) |
| 63 | COOCH(CH$_3$)COOC$_2$H$_5$ | CHF$_2$ | F | Cl | O | nD 1.5212(14.1° C.) |
| 64 | COOCH$_2$C≡CH | CHF$_2$ | Cl | Cl | O | m.p. 78.5° C. |
| 65 | COOCH$_3$ | CHF$_2$ | Cl | Cl | O | m.p. 63.9° C. |
| 66 | COOCH$_3$ | CHF$_2$ | F | Cl | O | m.p. 1.5430(17.0° C.) |
| 67 | COOC$_2$H$_5$ | CH$_3$ | Cl | Cl | S | m.p. 1.6029(20.1° C.) |
| 68 | COOC$_2$H$_5$ | CHF$_2$ | Cl | Cl | O | nD 1.5446(26.8° C.) |
| 69 | COOC$_2$H$_5$ | CHF$_2$ | F | Cl | O | nD 1.5320(21.0° C.) |
| 70 | OCH$_2$CH=CH$_2$ | CHF$_2$ | Cl | Cl | NH | m.p. 80.6° C. |
| 71 | OCH$_2$C≡CH | CHF$_2$ | Cl | Cl | NH | m.p. 118.9° C. |
| 72 | OCH$_2$COOCH$_3$ | i-C$_3$H$_7$ | Cl | Cl | — | Paste |
| 73 | OCH$_2$CH=CH$_2$ | i-C$_3$H$_7$ | Cl | Cl | — | Paste |
| 74 | OCH$_2$C≡CH | i-C$_3$H$_7$ | Cl | Cl | — | Paste |
| 75 | SCH$_2$COOCH$_3$ | t-C$_4$H$_9$ | Cl | Cl | — | Paste |
| 76 | OCH$_2$CH=CH$_2$ | CH$_2$Br | Cl | Cl | — | Paste |

Among the 3-substituted phenylpyrazole derivatives of the present invention represented by the general formula (I-1), preferred is the compound No. 19.

On the other hand, as the organophosphorus herbicidal compounds used in the present invention, the following can be referred to:

N-(phosphonomethyl)glycine or salts thereof, such as N-(phosphonomethyl)glycine isopropylamine salt (hereinafter, referred to as "Compound A"), or ammonium salt thereof or N-(phosphonomethyl)glycine trimethyl-sulfonium salt (hereinafter, referred to as "Compound B");

4-[hydroxy(methyl)phosphino]-DL-homoalanine or salts thereof such as 4-[hydroxy(methyl)phosphino]-DL-homoalanine ammonium salt (hereinafter, referred to as "Compound C");

4-[hydroxy(methyl)phosphino]-L-homoalanyl-L-alanyl-L-alanine or salts thereof, such as 4-[hydroxy-(methyl) phosphino]-L-homoalanyl-L-alanyl-L-alanine sodium salt (hereinafter, referred to as "Compound D"); etc.

Among these organophosphorus herbicidal compounds, preferred is N-(phosphonomethyl)glycine isopropylamine salt.

As the ethylenediamine alkoxylates used as a surfactant in this invention, the compounds represented by the following general formula (II):

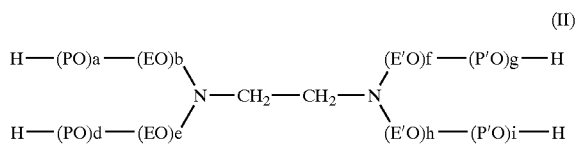

(II)

wherein EO represents —O—CH$_2$CH$_2$—, PO represents —O—CH(CH$_3$)CH$_2$—, E'O represents —CH$_2$CH$_2$—O—; P'O represents —CH$_2$(CH$_3$)CH—O— and a, b, d, e, f, g, h, and i represent integers of 1 to 20 which may be the same or different, can be referred to. As preferable examples thereof, Teric 170 (manufactured by Huntsman Co.) and Teric 173 (manufactured by the same company as above) can be referred to. One or more species of the above-mentioned ethylenediamine alkoxylates may be selected and put to use.

As the alcohol alkoxylates used in this invention, the compounds represented by the following general formula (III) can be referred to:

$C_kH_{2k+1}$—(EO)$_j$(PO)$_l$—OH (III)

wherein EO represents —O—CH$_2$CH—; PO represents —O—CH(CH$_3$)CH$_2$—; and k and l represent an integer of 1 to 20 which may be the same or different. Preferable examples of such compounds include the following: Noigen ET-165 (manufactured by Daiichi Kogyo Seiyaku K.K.), Adekatol SO-135 (manufactured by Asahi Denka K.K.), Noigen ET-115 (manufactured by Daiichi Kogyo Seiyaku K.K.), NK (Newkalgen)-D-1107S (manufactured by Takemoto Yushi K.K.), Lutensol T08 (manufactured by BASF Co.), TO-347 (manufactured by Nippon Nyuukazai K.K.), etc. One or more species of such alcohol alkoxylates may be selected and put to use.

In the herbicidal composition of the present invention, compounding ratios of the ingredients are as follows. That is, in 100 parts by weight of the herbicidal composition, the light-induced herbicidal compound is used in an amount of 0.01–10.0 parts by weight and preferably 0.1–2.0 parts by weight; the organophosphorus herbicidal compound is used in an amount of 1.0–60.0 parts by weight and preferably 5.0–40.0 parts by weight; the ethylenediamine alkoxylate is used in an amount of 0.1–25 parts by weight and preferably 10–25 parts by weight; and the alcohol alkoxylate is used in an amount of 0.1–15.0 parts by weight and preferably 0.1–5.0 parts by weight.

When the herbicidal composition of the present invention is put to use, the composition is made into an appropriate preparation form in accordance with the purpose according to the conventional method in the pesticide preparation, and then put to use. For instance, the composition is blended with a solid carrier, a liquid carrier or other necessary adjuvants, and the blended mixture thus obtained is made into a preparation form such as a suspension concentrate in which the active ingredient exists in the state of suspended fine particles, or a wettable powder, or a water dispersible granule, or the like and then put to use.

Further, it is also possible, if desired, to blend the composition of the present invention with an emulsifier comprising the same surfactant as used in the present invention in an amount of 0.1–99.0 parts by weight and preferably 25.0–75.0 parts by weight per part by weight of the light-induced herbicide compound of general formula (I), and a commercially available preparation containing an organophosphorus compound as an active ingredient thereof, at the time of preparing a liquid preparation to be sprayed, and thereafter to put to use.

When using a suspension concentrate or a water dispersible granule which contains, as the active ingredients thereof, a finely pulverized material comprising 0.01–10 parts by weight of the light-induced herbicidal compound represented by the general formula (I) without surfactant, and 1–50 parts by weight of an organophosphorus herbicidal compound; it is also possible, if desired, to make the same surfactant as used in this invention into a solution elsewhere and to mix the resulting solution with the suspension concentrate or water dispersible granule of this invention at the time of preparing a liquid mixture to be sprayed, at a ratio of 10–90 parts by weight of the surfactant solution per part by weight of the light-induced herbicidal compound represented by the general formula (I).

EXAMPLES

Next, typical examples and test examples of the present invention will be presented below. This invention is by no means limited by these examples.

As used in the examples, the term "part" and "parts" are by weight.

(Base)

| | |
|---|---|
| Compound No. 19 | 40.0 parts |
| Neocol YSK (manufactured by Daiichi Kogyo Seiyaku) | 1.0 part |
| Sorpol 7425 (Manufactured by Toho Kagaku Kogyo) | 3.0 parts |
| Propylene glycol | 3.0 parts |
| Silicone KM-73 (manufactured by Shin'etsu Kagaku) | 0.5 part |
| Proxel GXL (manufactured by Zeneca Japan) | 0.1 part |
| Rhodopol 23 (manufactured by Rhodia Nikka) | 0.02 part |
| Water | Balance |
| Total | 100 parts |

Each of the mixtures having the above-mentioned compounding ratios was finely pulverized by means of Dyno-Mill (manufactured by Bachofen AG) filled with 0.3 mm ceramic beads (Toreceram, manufactured by Toray K.K.) to prepare a suspension composition containing 40% of Compound No.19 as fine particles having a mean particle diameter of 0.3 μm.

Using the suspension concentrate thus obtained as a base, the compositions of the following Examples 1–12 were prepared.

Example 1

| | |
|---|---|
| Base of Compound No. 19 (40.0%) | 0.41 part |
| Compound A (62.0% aqueous solution) | 50.80 parts |
| Teric 170 | 10.00 parts |
| Noigen ET-165 | 2.00 parts |
| Propylene glycol | 2.50 parts |
| Soprophor DSS/7-60 (dispersant; manufactured by Rhodia Nikka Co.) | 0.83 part |
| N-Methylpyrrolidone (solvent) | 0.15 part |
| Silicone KM-73 (antifoaming agent) | 0.50 part |
| Proxel GXL (preservative) | 0.10 part |
| Attagel 50 (thickener; manufactured by Neolite Kosan) | 10.0 parts |
| Rhodopol 23 (thickener) | 0.10 part |
| Water | Balance |
| Total | 100.00 parts |

A mixture of the above-mentioned formulation was thoroughly homogenized by means of a mixer such as Auto-homomixer (manufactured by Tokushu Kika K.K.) or the like to obtain a suspension concentrate containing 0.15% of Compound No.19 and 30% of Compound A.

Examples 2–12

Suspension concentrate were prepared by repeating Example 1, except that the ethylenediamine alkoxylate, alcohol alkoxylate and organophosphorus herbicidal compound used in Example 1 were replaced with those shown in Table 2.

TABLE 2

| Example No. | Organophosphorus herbicidal compound Ethylenediamine alkoxylate Alcohol alkoxylate | Compounding ratio (parts by wt.) |
|---|---|---|
| 2 | Compound A | 30.00 |
| | Teric 170 | 10.00 |
| | Adekatol SO-135 (HLB = 13) | 2.00 |
| 3 | Compound A | 30.00 |
| | Teric 170 | 10.00 |
| | Noigen ET-115 (HLB = 11) | 2.00 |
| 4 | Compound A | 30.00 |
| | Teric 170 | 10.00 |
| | NK (Newkalgen) D-1107S | 2.00 |
| 5 | Compound A | 30.00 |
| | Teric 170 | 10.00 |
| | Lutensol TO8 (HLB = 13) | 2.00 |
| 6 | Compound A | 30.00 |
| | Teric 170 | 10.00 |
| | TO-347 | 2.00 |
| 7 | Compound A | 30.0 |
| | Teric 173 | 10.00 |
| | Noigen ET-165 (HLB = 216) | 2.00 |
| 8 | Compound A | 30.0 |
| | Teric 173 | 10.00 |
| | Adekatol SO-135 | 2.00 |
| 9 | Compound A | 30.0 |
| | Teric 173 | 10.00 |
| | Noigen ET-115 | 2.00 |

TABLE 2-continued

| Example No. | Organophosphorus herbicidal compound Ethylenediamine alkoxylate Alcohol alkoxylate | Compounding ratio (parts by wt.) |
|---|---|---|
| 10 | Compound B | 30.0 |
| | Teric 173 | 10.00 |
| | NK-D-1107S | 2.00 |
| 11 | Compound C | 30.0 |
| | Teric 173 | 10.00 |
| | Lutensol TO8 | 2.00 |
| 12 | Compound D | 30.0 |
| | Teric 173 | 10.00 |
| | TO-347 | 2.00 |

Comparative Example 1

A commercial preparation containing Compound A as an active ingredient (glyphosate isopropylamine salt solution) was used.

Comparative Example 2

A composition was prepared by repeating Example 1, except that the ethylenediamine alkoxylate was not used and the amount of the alcohol alkoxylate was altered from 2 parts to 12 parts.

Comparative Example 3

A composition was prepared by repeating Example 1, except that the alcohol alkoxylate was not used and the amount of the ethylenediamine alkoxylate was altered from 10 parts to 12 parts.

Test Example 1

Barnyard grass (*Echinochloa crus-galli*) and cocklebur (*Xanthium strumarium*) were cultured in a plastic-made pot having a diameter of 12 cm. When the plants had reached 7-leaved stage or a later stage, a test agent solution adjusted to a prescribed concentration was sprayed, and the herbicidal effect was visually evaluated by the naked eye on the third day and twenty first day after the treatment (0: no herbicidal effect; 100: withering).

The results are summarized in Table 3.

TABLE 3

| | Compound (g/ha) | | 3 days after | | 21 days after | |
|---|---|---|---|---|---|---|
| Example No. | 19 | Phosphorous type | Barnyard grass | Cocklebur | Barnyard grass | Cocklebur |
| 1 | 5 | 1000 | 68 | 85 | 100 | 100 |
| 2 | 5 | 1000 | 65 | 85 | 100 | 100 |
| 3 | 5 | 1000 | 60 | 85 | 100 | 100 |
| 4 | 5 | 1000 | 65 | 85 | 100 | 100 |
| 5 | 5 | 1000 | 68 | 83 | 100 | 100 |
| 6 | 5 | 1000 | 63 | 85 | 100 | 100 |
| 7 | 5 | 1000 | 65 | 85 | 100 | 100 |
| 8 | 5 | 1000 | 68 | 85 | 100 | 100 |
| 9 | 5 | 1000 | 68 | 83 | 100 | 100 |
| 10 | 5 | 1000 | 65 | 80 | 100 | 100 |
| 11 | 5 | 1000 | 68 | 83 | 100 | 100 |
| 12 | 5 | 1000 | 65 | 85 | 100 | 100 |
| Comparative Example 1 | 0 | 1000 | 20 | 20 | 85 | 100 |
| Comparative Example 2 | 5 | 1000 | 65 | 85 | 90 | 85 |

TABLE 3-continued

| Example No. | Compound (g/ha) | | 3 days after | | 21 days after | |
|---|---|---|---|---|---|---|
| | 19 | Phosphorous type | Barnyard grass | Cocklebur | Barnyard grass | Cocklebur |
| Comparative Example 3 | 5 | 1000 | 20 | 40 | 80 | 85 |

It has been found that, in a composition comprising a mixture of light-induced herbicidal compound, especially a 3-substituted phenylpyrazole derivative, and an organophosphorus herbicidal compound, an excellent rapid herbicidal action and an improvement of the herbicidal effect can be achieved by incorporating an ethylenediamine alkoxylate and an alcohol alkoxylate into the composition.

What is claimed is:

1. A herbicidal composition containing one or more compounds selected from light-induced herbicidal compounds and one or more compounds selected from organophosphorus herbicidal compounds as active ingredients thereof, characterized by containing an ethylenediamine alkoxylate and an alcohol alkoxylate as surfactants.

2. A herbicidal composition according to claim 1, wherein said light-induced herbicidal compound is a compound represented by the following general formula (I):

$$P-Q \qquad (I)$$

wherein P represents any one of $P^1$ to $P^9$:

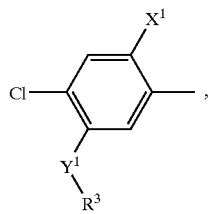
P¹

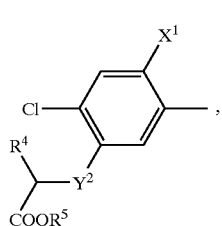
P²

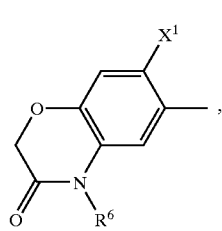
P³

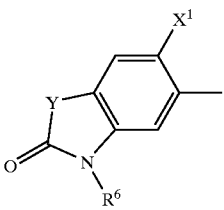
P⁴

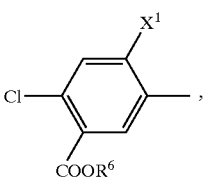
P⁵

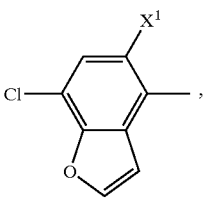
P⁶

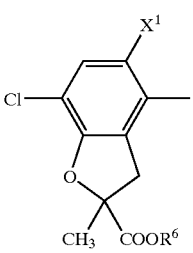
P⁷

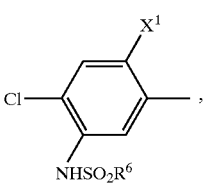
P⁸

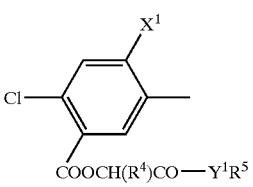
P⁹ wherein $X^1$, Y, $Y^1$, $Y^2$, $R^3$, $R^4$, $R^5$ and $R^6$ are as defined later, and Q represents any one of $Q^1$ to $Q^{11}$:

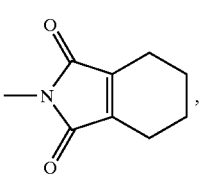
Q¹

-continued

Q² 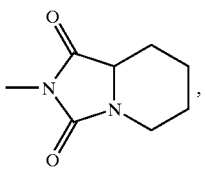

Q³ 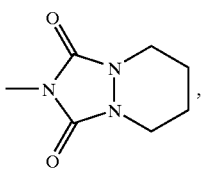

Q⁴ 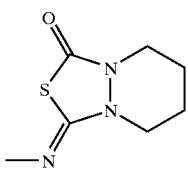

Q⁵ 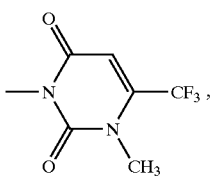

Q⁶ 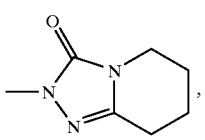

Q⁷ 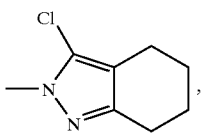

Q⁸ 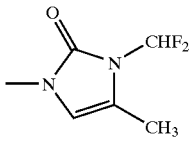

Q⁹ 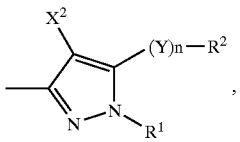

Q¹⁰ 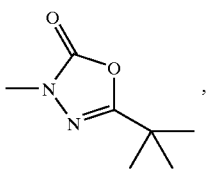

-continued

Q¹¹ 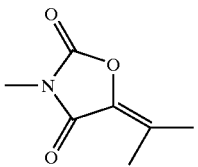

wherein $R^1$ represents a $(C_1-C_6)$ alkyl group; $R^2$ represents a hydrogen atom, a $(C_1-C_6)$ alkyl group or a halo $(C_1-C_6)$ alkyl group; $R^3$ represents a $(C_1-C_6)$ alkyl group, a halo $(C_1-C_6)$ alkyl group, a $(C_3-C_6)$ cycloalkyl group, a $(C_2-C_6)$ alkenyl group or a $(C_2-C_6)$ alkynyl group; $R^4$ represents a hydrogen atom or a $(C_1-C_6)$ alkyl group; $R^5$ represents a hydrogen atom, a $(C_1-C_6)$ alkyl group, a halo $(C_1-C_6)$ alkyl group, a $(C_2-C_6)$ alkenyl group or a $(C_2-C_6)$ alkynyl group; $R^6$ represents a $(C_1-C_6)$ alkyl group, a $(C_2-C_6)$ alkenyl group or a $(C_2-C_6)$ alkynyl group; $X^1$ and $X^2$ represent halogen atoms which may be the same or different; Y represents —O—, —S—, —SO— or —SO$_2$—; $Y^1$ represents —O— or —S—; $Y^2$ represents —O—, —S— or —NH—; and n represents an integer of 0 to 1.

3. A herbicidal composition according to claim 1, wherein said light-induced herbicidal compound is one or more compounds selected from the substituted phenylpyrazole derivatives represented by the following general formula (I-1):

(I-1)

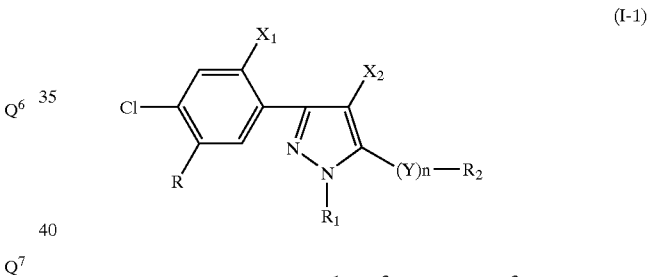

wherein R represents —$Y^1$—$R^3$ (wherein $R^3$ represents a $(C_1-C_6)$ alkyl group, a halo $(C_1-C_6)$ alkyl group, a $(C_2-C_6)$ alkenyl group or a $(C_2-C_6)$ alkynyl group and $Y^1$ represents —O— or —S—), —$Y^2$CH($R^4$)CO—O$R^5$ (wherein $R^4$ represents a hydrogen atom or a $(C_1-C_6)$ alkyl group, $R^5$ represents a hydrogen atom, a $(C_1-C_6)$ alkyl group, a halo $(C_1-C_6)$ alkyl group, a $(C_2-C_6)$ alkenyl group or a $(C_2-C_6)$ alkynyl group, and $Y^2$ represents —O—, —S— or —NH—), —COOCH($R^4$)CO—$Y^1$—$R^5$ (wherein $R^4$, $R^5$ and $Y^1$ are as defined above) or —COO$R^6$ (wherein $R^6$ represents a $(C_1-C_6)$ alkyl group, a $(C_2-C_6)$ alkenyl group or a $(C_2-C_6)$ alkynyl group); $R^1$ represents a $(C_1-C_6)$ alkyl group; $R^2$ represents a hydrogen atom, a $(C_1-C_6)$ alkyl group or a halo $(C_1-C_6)$ alkyl group; $X^1$ and $X^2$ represent halogen atoms which may be the same or different; Y represents —O—, —S—, —SO— or —SO$_2$—; and n represents an integer of 0 to 1.

4. A herbicidal composition according to claim 1, wherein said organophosphorus herbicidal compound is N-(phosphonomethyl)glycine or a salt thereof, 4-[hydroxy(methyl)phosphino]-DL-homoalanine or a salt thereof, or 4-[hydroxy(methyl)phosphino]-L-homoalanyl-L-alanyl-L-alanine or a salt thereof.

5. A herbicidal composition according to claim 1, wherein said ethylenediamine alkoxylate is one or more compounds selected from the compounds represented by the following general formula (II):

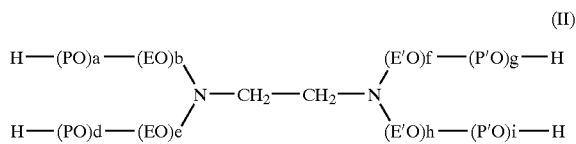
(II)

wherein EO represents —O—CH$_2$CH$_2$—; PO represents —O—CH(CH$_3$)CH$_2$—; E'O represents —CH$_2$CH$_2$—O—; P'O represents —CH$_2$(CH$_3$)CH—O—; and a, b, d, e, f, g, h and i represent integers of 1 to 20 which may be the same or different.

6. A herbicidal composition according to claim 5, wherein said ethylenediamine alkoxylate is an adduct of ethylenediamine and polyoxyethylene, an adduct of ethylenediamine and polyoxypropylene or an adduct of ethylenediamine and a polyoxyethylene-polyoxypropylene copolymer.

7. A herbicidal composition according to claim 1, wherein said alcohol alkoxylate is one or more compounds selected from the compounds represented by the following general formula (III):

$C_kH_{2k+1}$—(EO)$_j$(PO)$_l$—OH    (III)

wherein EO represents —O—CH$_2$CH$_2$—; PO represents —O—CH(CH$_3$)CH$_2$—; and j, k and l represent zero or integers of 1 to 20 which may be the same or different, provided that both of j and l do not indicate zero at the same time.

8. A herbicidal composition according to claim 7, wherein said alcohol alkoxylate is a mixture of one or more compounds selected from the group consisting of primary alcohol ethoxylate, primary alcohol propoxylate, primary alcohol ethoxylate propoxylate, secondary alcohol ethoxylate, secondary alcohol propoxylate, secondary alcohol ethoxylate propoxylate, tertiary alcohol ethoxylate, tertiary alcohol propoxylate and tertiary alcohol ethoxylate propoxylate.

9. A herbicidal composition according to claim 1, which contains one or more compounds selected from light-induced herbicidal compounds in an amount of 0.01–10 parts by weight, an organophosphorus herbicidal compound in an amount of 1–60 parts by weight, an ethylenediamine alkylate in an amount of 0.1–25 parts by weight and an alcohol alkoxylate in an amount of 0.1–15 parts by weight, all per 100 parts by weight of the herbicidal composition.

10. A herbicidal composition according to claim 1, wherein said herbicidal composition is a suspension concentrate, a water dispersible granule or an aqueous preparation.

11. A method for using a herbicidal composition characterized by treating the objective weed or the soil with an effective amount of the herbicidal composition according to claim 1 for the purpose of controlling the weeds harmful to crop plants.

* * * * *